United States Patent [19]

Mesens et al.

[11] Patent Number: 5,612,346
[45] Date of Patent: Mar. 18, 1997

[54] RISPERIDONE PAMOATE

[75] Inventors: Jean L. Mesens, Wechelderzande; Jozef Peeters, Beerse, both of Belgium

[73] Assignee: Janssen Pharmaceutica N.V., Beerse, Belgium

[21] Appl. No.: 522,422

[22] PCT Filed: Apr. 22, 1994

[86] PCT No.: PCT/EP94/01296

§ 371 Date: Sep. 22, 1995

§ 102(e) Date: Sep. 22, 1995

[87] PCT Pub. No.: WO94/25460

PCT Pub. Date: Nov. 10, 1994

[30] Foreign Application Priority Data

Apr. 28, 1993 [EP] European Pat. Off. .............. 93201216

[51] Int. Cl.$^6$ ...................... C07D 413/14; A61K 31/505
[52] U.S. Cl. ............................. 514/258; 544/282
[58] Field of Search .............................. 514/258; 544/282

[56] References Cited

U.S. PATENT DOCUMENTS 4,804,663  2/1989  Kennis et al. ........................ 514/258

Primary Examiner—Matthew V. Grumbling
Attorney, Agent, or Firm—Charles J. Metz

[57] ABSTRACT

A compound which is a pamoate acid addition salt of risperidone, compositions comprising the same and processes for preparing said compound and compositions.

7 Claims, No Drawings

RISPERIDONE PAMOATE

CROSS-REFERENCE TO RELATED APPLICATIONS

This application is based upon PCT application Ser. No. PCT/EP 94/01296, filed Apr. 22, 1994, which claims priority from European Patent Application Ser. No. 93.201.216.4, filed on Apr. 28, 1993.

EP-0,196,132 discloses the compound 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one, that is known genetically as risperidone and is a potent antipsychotic. Unfortunately, the current formulations of risperidone only yield effective plasma levels during a limited time interval. Long-acting injectable risperidone dosage forms would be valuable in maintenance therapy and would enhance patient compliance.

Currently available long-acting neuroleptics include solutions in oils, e.g. sesame oil, of poorly water-soluble ester derivatives of the neuroleptic compounds. Trials to prolong the activity of some particular phenothiazine neuroleptics by the use of poorly water-soluble salts such as the pamoates proved to be little successful (e.g. Florence et al., 1976, J. Pharm. Sci., 65(11), 1665–1668). Unexpectedly, the use of the pamoate salt of risperidone in dogs significantly prolonged the release of risperidone, yielding plasma levels of risperidone and its active metabolite that were effective against apomorphine induced emesis during several weeks.

Accordingly, the present invention is concerned with the pamoate acid addition salts of risperidone. In particular, the invention is concerned with the compound having the formula

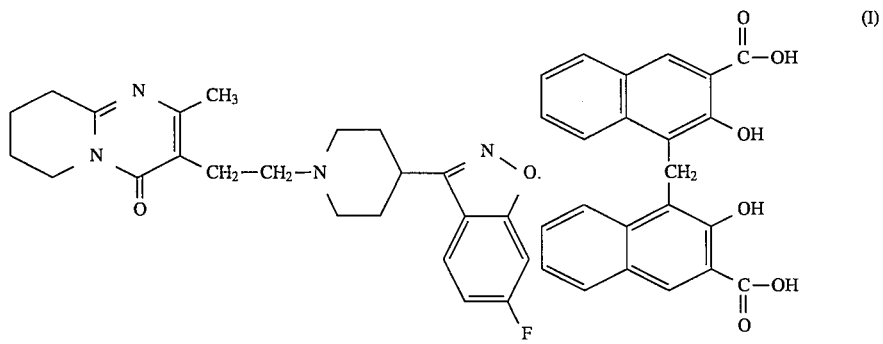

The period during which effective plasma levels are obtained depends on the physical characteristics of the risperidone pamoate powder sample, such as particle size and crystal form.

Risperidone, its preparation and the pharmacological activity thereof are described in EP-0,196,132. The pamoate salt of risperidone can be prepared by the treatment of risperidone with pamoic acid or a salt derivative thereof, e.g. the disodium pamoate, in a reaction-inert solvent. In particular, risperidone pamoate can be prepared by adding a solution of risperidone in an appropriate solvent, e.g. ethanol, to a solution of pamoic acid in an appropriate solvent, e.g. N,N-dimethylformamide, and stirring the mixture until precipitation of the risperidone pamoate salt. The reaction product may be isolated from the medium and, if necessary, further purified according to methodologies generally known in the art such as, for example, extraction, crystallization and chromatography. Micronized forms of the subject compounds can be prepared by micronization techniques known in the art, e.g. by milling in appropriate mills and sieving through appropriate sieves.

In a particular aspect, the invention relates to the mixed pamoate addition salts of risperidone, e.g. the monosodium pamoate salt of risperidone.

The subject compounds are potent antagonists of neurotransmitters and in particular of dopamine. Antagonizing said neurotransmitter suppresses a variety of phenomena induced by the release, in particular the excessive release, of dopamine. Central dopamine receptor blockers are known to have neuroleptic properties, for example, they counteract the positive symptoms of schizophrenia, e.g. hallucinations, delusional thinking, severe excitement and unusual behaviour. Therapeutic indications for using the present compound therefore are mainly in the CNS area, particularly as potent antipsychotic agents and especially as agents useful in treating chronic psychoses. The present compounds also show central serotonin antagonism. Central acting serotonin antagonists appear to improve the negative symptoms of schizophrenia, e.g. anergy, apathy, social withdrawal and depressive mood, and also to reduce the incidence of extrapyramidal side-effects (EPS) during maintenance therapy with classical neuroleptics, i.e. dopamine antagonists. Combined dopamine-serotonin antagonists are especially interesting as they offer relief of both the positive and negative symptoms of schizophrenia with low EPS liability.

The subject compounds show the advantage of being long acting dopamine antagonists by the sustained release of risperidone from the poorly water-soluble pamoate salts. This can be evidenced, for example, by measuring the plasma levels after intramuscular or subcutaneous administration to dogs and by the long acting antiemetic effect exerted by the present compounds on dogs challenged with the dopamine agonist apomorphine. Hence, the subject compounds allow administration at relatively large intervals, e.g. at several weeks, the actual time of administration depending on the physical nature of the compound used and the condition of the subject to be treated. Consequently, the present compounds allow for a more efficient therapy: the sustained release facilitates maintaining a stable plasma concentration at a non-toxic, effective level and the route of administration enhances compliance of the subject to be treated with the prescribed medication.

Unlike most of the currently available long-acting neuroleptics which are usually formulated in an oil for intramuscular administration, the subject compounds show the advantage that they can be formulated in both lipophilic (e.g. an oil) and lipophobic solvents (e.g. aqueous environment) and may be administered in various ways, e.g. intramuscularly or subcutaneously.

In view of their useful pharmacological properties, the subject compounds may be formulated into various pharmaceutical forms for administration purposes. To prepare the pharmaceutical compositions of this invention, an effective amount of the subject compounds as the active ingredient is combined in intimate admixture with a pharmaceutically acceptable carder, which carder may take a wide variety of forms depending on the form of preparation desired for administration. These pharmaceutical compositions are desirably in unitary dosage form suitable, preferably, for administration subcutaneously or intramusculary. For the latter administration routes, the subject compounds preferably are suspended in an aqueous solvent, which may further comprise a wetting agent, such as the polyoxyethylene derivatives of sorbitan esters, e.g. polysorbate 80 (=Tween 80®) and polysorbate 20 (=Tween 20®), lecithin, polyoxyethylene- and polyoxypropylene ethers, sodium deoxycholate, and the like; a suspending agent such as a cellulose derivate, e.g. methylcellulose, sodium carboxymethylcellulose and hydroxypropyl methylcellulose, polyvinylpyrrolidone, alginates, chitosan, rextrans, gelatin, polyethylene glycols, polyoxyethylene- and polyoxypropylene ethers and the like; an acid, e.g. hydrochloric acid, and the like; a base, e.g. sodium hydroxide, and the like; a buffer comprising a mixture of appropriate amounts of an acid such as phosphoric, succinic, tartaric, lactic, acetic, maleic or citric acid, and a base, in particular sodium hydroxide or disodium hydrogen phosphate; a preservative, e.g. benzoic acid, benzyl alcohol, butylated hydroxyanisole, butylated hydroxytoluene, chlorbutol, a gallam, a hydroxybenzoate, EDTA, phenol, chlorocresol, metacresol, benzothonium chloride, myristyl-γ-piccolinium chloride, phenylmercuri acetate, thimerosal and the like; a tonicity adjusting agent, e.g. sodium chloride, dextrose, mannitol, sorbitol, lactose, sodium sulfate, and the like Alternatively, the subject compounds may be formulated in an oil. Appropriate oils for this purpose are fixed oils, for example, peanut oil, sesame oil, cottonseed oil, corn oil, safflower oil, castor oil, ethyloleate, soy bean oil, synthetic glycerol esters of long chain fatty or medium chain acids and mixtures of these and other oils.

Also thickening agents may be added to the composition, e.g. aluminum monostearate, ethylcellulose, triglycerides, hydrogenareal castor oil, and the like.

In view of the usefulness of the subject compounds in the treatment of psychotic diseases it is evident that the present invention provides a method of treating warm-blooded animals, in particular humans, suffering from psychotic diseases, said method comprising the administration of a pharmaceutically effective amount of the subject compounds in admixture with a pharmaceutical carder. In a further aspect, the present invention relates to the use of the subject compounds as a medicine, particularly as an antipsychotic. In general it is contemplated that an effective amount would be from 0.05 mg/kg to 50 mg/kg body weight, more preferably from 0.5 mg/kg to 10 mg/kg body weight.

The following examples are intended to illustrate and not to limit the scope of the present invention.

EXAMPLE 1

A solution of 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one (0.048 mol) in ethanol (600 ml) was added to a solution of pamoic acid (0.048 mol) in N,N-dimethylformamide (400 ml). The mixture was stirred for 3 hours. The resulting precipitate was filtered off by suction, washed with ethanol and dried, yielding 31 g (81%) of 3-[2-[4-(6-fluoro-1,2-benzisoxazol-3-yl)-1-piperidinyl] ethyl]-6,7,8,9-tetrahydro-2-methyl-4H-pyrido[1,2a]pyrimidin-4-one 4,4'-methylenebis[3-hydroxy-2-naphthalenecarboxylate] (1:1); mp. 269.2° C.

EXAMPLE 2

F1: aqueous suspension

| risperidone monopamoate | 25 mg |
| polysorbate 20 | 1 mg |
| benzyl alcohol | 10 mg |
| purified water | q.s. 1 ml |

The risperidone monopamoate, polysorbate 20, benzyl alcohol and purified water were intimately mixed and homogenized, thus yielding an aqueous suspension.

In a similar way there were prepared:

F2: aqueous suspension

| risperidone monopamoate | 50 mg |
| polysorbate 20 | 2 mg |
| benzyl alcohol | 15 mg |
| sodium carboxymethylcellulose | 20 mg |
| purified water | q.s. 1 ml |

F3: suspension in oil

| risperidone monopamoate | 50 mg |
| sesame oil | q.s. 1 ml |

EXAMPLE 3

The prolonged action of the risperidone monopamoate salt over the risperidone free base was established by the following procedure The apomorphine test in dogs The method used is described by P. A. J. Janssen and C. J. E. Niemegeers in Arzneim.-Forsch. (Drug Res.), 9, 765–767 (1959). A suspension of the risperidone free base in sesame oil and the risperidone monopamoate compositions F1, F2 and F3 were administered to 3 beagle dogs at a dose between 2 and 2.5 mg/kg. The risperidone free base formula as well as F1 and F3 were administered intramuscularly, whereas F2 was administered subcutaneously. At several time intervals thereafter, the animals were challenged with a standard dose of 0.31 mg/kg (subcutaneous) of apomorphine, which is a potent dopamine agonist and induces emesis. The antiemetic effect of the test compound was used as an indication of its activity.

The table hereinbelow summarizes the mean period of activity (days) that was obtained in the 3 test animals.

| | Mean period of activity (days) |
| --- | --- |
| Risperidone in sesame oil | 3 |
| F1 | 22 |
| F2 | 18 |
| F3 | 12 |

From the table it is clear that the administration of risperidone pamoate resulted in a significantly longer period of activity when compared to the administration of the risperidone free base.

We claim:

1. A compound which is a pamoate acid addition salt of risperidone.

2. A compound according to claim 1 having the formula

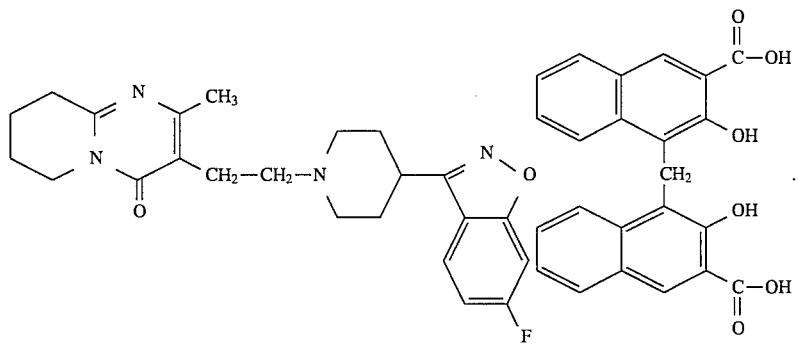

3. A composition comprising a pharmaceutically acceptable carrier and as active ingredient a pharmaceutically effective amount of a compound as claimed in claim 1.

4. A composition according to claim 3 in an injectable dosage form.

5. A composition according to claim 4 which takes the form of an aqueous suspension.

6. A composition according to claim 5 further comprising benzyl alcohol, a sorbitan ester and water.

7. A composition according to claim 6 further comprising a cellulose derivative.

* * * * *